Figure 1:
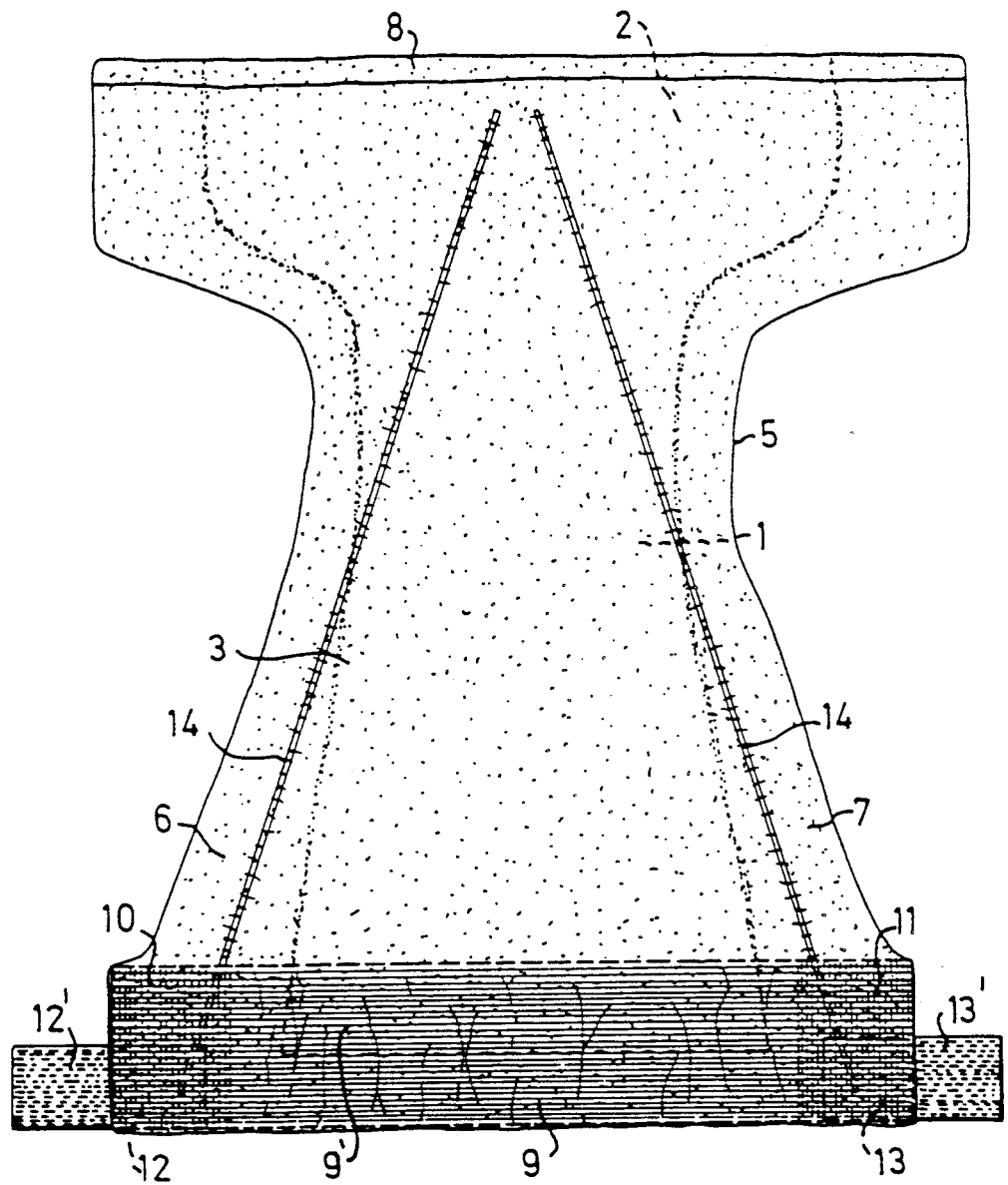

United States Patent [19]

Björksund et al.

[11] Patent Number: 4,998,929

[45] Date of Patent: Mar. 12, 1991

[54] DISPOSABLE DIAPER

[75] Inventors: Margareta Björksund, Falkenberg; Urban Widlund, Mölnlycke, both of Sweden

[73] Assignee: Molnlycke AB, Gothenburg, Sweden

[21] Appl. No.: 449,372

[22] Filed: Dec. 6, 1989

Related U.S. Application Data

[63] Continuation of Ser. No. 175,388, Feb. 19, 1988, abandoned.

[30] Foreign Application Priority Data

Jul. 17, 1986 [SE] Sweden .............................. 8603154-9

[51] Int. Cl.$^5$ ............................................. A61F 13/16
[52] U.S. Cl. .................................. 604/385.2; 604/398
[58] Field of Search ...................... 604/370, 378, 385.1, 604/385.2, 398; 2/402, 403, 406

[56] References Cited

U.S. PATENT DOCUMENTS

| | | | |
|---|---|---|---|
| 3,461,872 | 8/1969 | McConnell et al. | 604/385.2 |
| 3,658,064 | 4/1972 | Pociluyko | 604/385.2 |
| 3,990,450 | 11/1976 | Schaar . | |
| 4,024,867 | 5/1977 | Mesek . | |
| 4,704,114 | 11/1987 | Wilson et al. | 604/385.1 |

FOREIGN PATENT DOCUMENTS

| | | |
|---|---|---|
| 0206208 | 12/1986 | European Pat. Off. . |
| 3238450 | 5/1983 | Fed. Rep. of Germany . |
| 2462112 | 2/1981 | France . |
| 2095561 | 10/1982 | United Kingdom . |

Primary Examiner—John D. Yasko
Assistant Examiner—A. Gutowski
Attorney, Agent, or Firm—Young & Thompson

[57] ABSTRACT

Disposable diapers comprising an absorbent body (1) which is surrounded by a casing consisting of a liquid permeable outer layer (3) facing the wearer during use of the diaper, and a liquid impermeable outer layer disposed on the opposite side of the absorbent body. The distinguishing feature of the invention is that an elastic waist means in the form of a comparatively wide elastic strip (9) extending in the transverse direction of the diaper is applied in a prestretched state at least at one end portion of the diaper, said strip being connected via an edge portion with the liquid impermeable outer layer while being arranged to constitute, together with said outer layer, a liquid absorbing pocket sealing around the end portion of the absorbent body.

5 Claims, 2 Drawing Sheets

DISPOSABLE DIAPER

This application is a continuation of application Ser. No. 175,388, filed 2/19/99, which is now abandoned.

The present invention relates to a disposable diaper comprising an absorbent body, preferably of cellulose fluff pulp, surrounded by a casing composed of a liquid-permeable outer layer of fiber fabric for example, which faces the wearer during use of the diaper, and a liquid impermeable outer layer on the opposing side of the absorbent body, said two outer layers being joined together around the absorbent body, as well as elastic means sealing around the wearer's legs and waist; so-called leg and waist elastic, respectively.

In normal cases, disposable diapers of this kind are designed with a narrow crotch portion and with end portions having substantially wider dimensions in relation to said crotch portion and being referred to in the following as the belly portion and the bottom portion, respectively. Together with the narrow crotch portion, these two wider portions are made to seal around the wearer's abdomen. The bottom portion is provided with attachment tabs which, when the diaper is put on, are secured to the outside of the belly portion by means of areas coated with adhesive As a result, the diaper when put on will obtain a pant-like shape, all additional attachment aids such as diaper backing sheets or plastic pants thereby being superfluous Serious problems are caused by leakage occurring about the wearer's legs and waist, although such leakage has to a substantial degree been eliminated by the application of so-called leg and waist elastic, serving to retain the diaper in tightly sealing contact with the waist and leg portions of the wearer's body.

In order to maintain the fit of the diaper during use, and to hold the elastic means tightly sealed to the wearer's body, there is however required a comparatively high degree of elasticity, which will give rise to sores on the wearer's skin due to chafing.

In the teaching of previously known diapers using elastic bands or threads as elastic waist means, there is still lacking a satisfactory solution to the problem of leakage around the waist portion because the contracting force of the elastic means must be only insignificant in order to avoid skin irritation due to chafing but which many times results in the formation of gaps between the elastic seals and the wearer's skin, the risk of waist leakage then being especially great when the wearer is lying on his back. Admittedly, prior art technique also teaches the manner of folding the liquid impermeable layer incorporated in the diaper casing over the end edges of the absorbent body and a distance in over the liquid permeable layer of the casing which faces the wearer's body during use of the diaper. Although leakage coming from the absorbent body itself is thereby avoided per se, discharged liquid cannot be prevented from running on the inside of the diaper and out through the gaps occurring between the diaper and the belly and bottom of the wearer. Even if the liquid-tight plastic layer forming part of the diaper casing is folded around the end edges of the absorbent body, there would still be required some kind of elastic waist means. Conventional folding of the liquid-tight plastic layer further involves the drawback that the plastic layer in question will necessarily seal tightly to the absorbent body at the site of folding since with this folding method, the end edges of the absorbent body must serve as folding edges, which is a factor restricting the design of the diaper at the end edges thereof. Up to now, there has been found no successful combination of such folding and a satisfactorily functioning elastic waist means.

Also available on the market are diapers having individual plastic strips applied across the width of the diaper at the end portion thereof. However, the design of these diapers corresponds in all essentials to the type employing the already mentioned prior art method of folding around the end edges of the absorbent body with the absorbent body extending substantially all the way up to the diaper end eges which is, as set forth above, difficult to combine with a suitable waist elastic.

With the present invention, however, there has been achieved a disposable diaper by means of which the problems in question have been completely overcome.

For this propose, a disposable diaper performed in accordance with the invention is primarily characterized in that the elastic waist means consists of a relatively wide strip lying on the side of the absorbent body facing the wearer during use and extending across the width of at least one of the diaper end portions, said strip being made of an elastic and liquid-tight material such as polyurethane to advantage, which is applied in a prestretched state while being connected, via an edge portion located beyond the corresponding end of the absorbent body, to the liquid-impermeable outer layer for creating a liquid-tight pocket which seals around said end of the absorbent body.

In a preferred embodiment of the inventive diaper, the strip serving as an elastic waist means in combination with the two outer layers extends in the longitudinal direction of the diaper a distance beyond the absorbent body.

Figure 2:
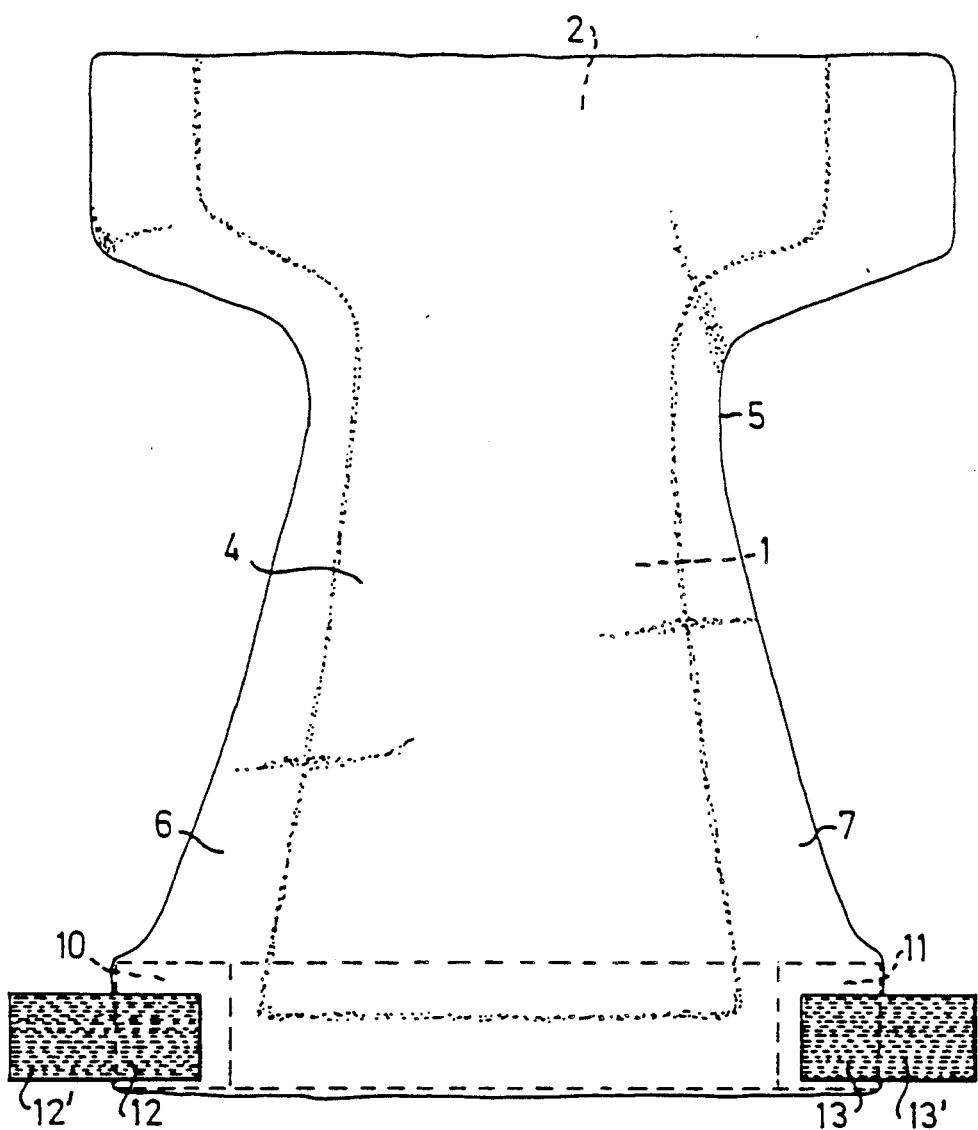

The invention will be more closely described in the following with reference to an exemplary embodiment illustrated in the accompanying drawings, of which FIG. 1 shows an embodiment of a diaper-performed in accordance with the invention in its flat, extended state as viewed from the side facing the wearer during use; the inside, whereas FIG. 2 shows the same diaper as viewed from the outside.

The diaper illustrated in the drawings has a T-shaped absorbent body 1 of cellulose fluff pulp. The wider portion thereof facing the wearer's belly has been designated by reference numeral 2. The absorbent body is enclosed in a casing composed of a liquid permeable layer 3 of fiber fabric which faces the wearer during use, and a liquid-tight plastic film 4 of polyethylene applied to the opposite side of the absorbent body. The casing extends laterally beyond the wide edges of the absorbent body, which is where the two layers incorporated in the casing are joined together. As can be seen from FIGS. 1 and 2, the two interconnected outer layers 3, 4 extend from the crotch portion 5 and rearwardly with a gradually increasing distance from the side edges of the absorbent body while forming side flaps 6, 7 intended to cover the wearer's bottom during use of the diaper. At the front edge portion 8 folded around the forward end portion of the absorbent body. The liquid permeable fiber fabric 3 extends across this folded plastic portion, since for the wearer's maximum comfort his skin should be protected from direct contact with plastic material.

At the opposing diaper end, the two casing layers 3, 4 extend, longitudinally beyond the absorbent body 1 where they are joined together. At this diaper end and on the inside of the liquid permeable fiber fabric layer 3, there is affixed a relatively wide strip 9 of an elastic and liquid impermeable material, suitably polyurethane, which extends across the width of the diaper. This strip 9, together with the two outer layers 3, 4 included in the casing, extends beyond the end edge of the absorbent body with one portion 9' continuing in over the absorbent body. In combination with the liquid impermeable outer layer 4, the strip 9 thus constitutes a liquid-tight pocket sealing around the end portion of the absorbent body.

The center portion of the strip 9 is connected with the two outer layers 3, 4 in a prestretched condition for creating an elastic waist means, whereas the two end portions 10, 11 thereof are connected in a non-stretched condition with said outer layers. Incorporated in the diaper there are namely attachment members in the form of tape tabs 12, 13 affixed to the liquid-tight plastic film directly over the non-stretched end portions 10, 11 of the strip 9, and to this end it is important for said attachment tabs to be so applied to a non-stretched carrier that this carrier is not subjected to contraction thereby causing the attachment tabs to loose their grip.

The illustrated diaper also includes elastic bands or threads 14 applied under pretension in a V-shaped pattern over the diaper. This additional elastic means will cause the diaper side flaps 6, 7 to contract over the wearer's bottom, the diaper simultaneously being pulled at the apex of the V-shaped pattern towards the wearer's belly.

It should be carefully observed that the attachment tabs be affixed to the extension of the elastic waist means in order to ensure stretch thereof when applying the diaper, the tape portions 12', 13' thus being attached to the diaper front end, the belly portion, on the outside of the plastic film 4.

In the embodiment shown, the elastic waist means as well as the V-shaped elastic means will be stretched upon longitudinal pulling of the attachment tabs.

The invention is not restricted to the exemplary embodiment set forth above, since numerous modifications are conceivable within the scope of the patent claims.

We claim:

1. An elongated disposable diaper having opposite end portions, comprising an elongated absorbent body (1) having opposite ends, a casing surrounding the absorbent body and consisting of a liquid permeable outer layer (3) intended to face the wearer's body during use of the diaper, and a liquid impermeable outer layer (4) on the opposite side of the absorbent body, said two outer layers being joined together around the absorbent body, elastic means (9, 14) to seal around the wearer's legs and waist; the elastic waist means comprising a strip (9) of an elastic and liquid-tight material, which is applied in a prestretched state onto the bodycontacting side of the absorbent body between said layers (3, 4), said elastic strip extending across the width of at least one of said diaper end portions, said elastic strip having end portions (10, 11) and having an edge portion located beyond the adjacent said end of the absorbent body and an intermediate portion (9') between the end portions overlapping the adjacent end part of the absorbent body, said end portions (10, 11) of the elastic strip being located at opposite ends of said edge portion of said elastic strip, said elastic strip being connected via said edge portion and said end portions (10, 11) of the elastic strip to the liquid impermeable outer layer (4) both along said edge portion and laterally of said adjacent end of the absorbent body in said end portions (10, 11) of the elastic strip for creating a liquid-tight pocket in which said adjacent end of the absorbent body is disposed, one side of said pocket being comprised by said liquid impermeable outer layer and an opposite side of said pocket being comprised by said intermediate portion (9') of said elastic strip.

2. A diaper according to claim 1, characterized in that the strip (9) serving as an elastic waist means, together with the two outer layers (3, 4), extends in the longitudinal direction of the diaper a distance beyond the absorbent body (1).

3. A diaper according to claim 1, characterized in that the strip (9) extends laterally beyond the absorbent body (1) where it is connected over its entire area with the two outer layers.

4. A diaper according to claim 1, in which only the midportion of said strip (9) is prestretched and said end portions (10, 11) of said strip (9) are connected in a non-stretched condition to said outer layers (3, 4), and tape tabs (12, 13) secured to the liquid impermeable outer layer (4) directly over said end portions (10, 11) of said strip (9) for holding the diaper on a wearer.

5. A diaper according to claim 1, in which the material of said strip (9) is polyurethane.

* * * * *